(12) United States Patent
Riegel et al.

(10) Patent No.: US 8,314,173 B2
(45) Date of Patent: *Nov. 20, 2012

(54) METHOD FOR PRODUCING WHITE AND COLOR-STABLE WATER-ABSORBING POLYMER PARTICLES HAVING HIGH ABSORBENCY AND HIGH SALINE FLOW CONDUCTIVITY

(75) Inventors: Ulrich Riegel, Landstuhl (DE); Thomas Daniel, Waldsee (DE); Uwe Stueven, Bad Soden (DE); Mark Elliott, Ludwigshafen (DE); Volker Braig, Weinheim-Lützelsachsen (DE); Michael de Marco, Palo Alto, CA (US)

(73) Assignee: BASF SE, Ludwigshafen (DE)

( * ) Notice: Subject to any disclaimer, the term of this patent is extended or adjusted under 35 U.S.C. 154(b) by 239 days.

This patent is subject to a terminal disclaimer.

(21) Appl. No.: 12/521,953

(22) PCT Filed: Jan. 29, 2008

(86) PCT No.: PCT/EP2008/051010
§ 371 (c)(1),
(2), (4) Date: Jul. 1, 2009

(87) PCT Pub. No.: WO2008/092843
PCT Pub. Date: Aug. 7, 2008

(65) Prior Publication Data
US 2010/0041550 A1 Feb. 18, 2010

(30) Foreign Application Priority Data
Jan. 29, 2007 (EP) .................................... 07101342

(51) Int. Cl.
*C07F 7/00* (2006.01)

(52) U.S. Cl. ......................................... 524/329; 502/402
(58) Field of Classification Search ................... 524/329
See application file for complete search history.

(56) References Cited

U.S. PATENT DOCUMENTS

| | | | |
|---|---|---|---|
| 6,359,049 B1 * | 3/2002 | Carrico et al. ................. 524/414 |
| 6,620,889 B1 * | 9/2003 | Mertens et al. | |
| 2007/0161759 A1 * | 7/2007 | Riegel et al. ................... 525/375 |
| 2007/0293632 A1 * | 12/2007 | Riegel et al. ................ 525/329.9 |
| 2008/0171837 A1 | 7/2008 | Exner et al. | |
| 2008/0200583 A1 * | 8/2008 | Herth et al. .................... 522/171 |

FOREIGN PATENT DOCUMENTS

| | | | |
|---|---|---|---|
| DE | 10 2004 057 874 | | 6/2006 |
| WO | WO 00/55245 | | 3/2000 |
| WO | WO 00/53664 | | 9/2000 |
| WO | WO2005/054356 | | 6/2005 |
| WO | WO 2005/080479 | * | 9/2005 |
| WO | WO2006/015729 | | 2/2006 |
| WO | WO 2006/058682 | * | 6/2006 |
| WO | WO 2006/079462 | * | 8/2006 |

OTHER PUBLICATIONS

International Search Report in PCT/EP2008/051010 dated Aug. 4, 2009.

"Addition of Post-Treatments," Chapter 3.2.8. in *Modern Superabsorbent Polymer Tchnology*, 1998, 97-103, John Wiley & Sons, Inc., New York, New York.

* cited by examiner

*Primary Examiner* — Doris Lee
(74) *Attorney, Agent, or Firm* — Marshall, Gerstein & Borun LLP

(57) ABSTRACT

Water-absorbing polymeric particles are produced by polymerizing a monomer solution or suspension comprising at least one unsaturated carboxylic acid and at least one hydroquinone monoether, and coating the polymeric particles with at least one salt of a tervalent metal cation of a carboxylic acid and/or at least one basic salt of a tervalent metal cation.

22 Claims, No Drawings ated Jan. 29, 2007.

METHOD FOR PRODUCING WHITE AND COLOR-STABLE WATER-ABSORBING POLYMER PARTICLES HAVING HIGH ABSORBENCY AND HIGH SALINE FLOW CONDUCTIVITY

CROSS-REFERENCE TO RELATED APPLICATIONS

This is the U.S. national phase of International Application No. PCT/EP2008/051010, filed Jan. 29, 2008, which claims the benefit of European Patent Application No. 07101342.9, filed Jan. 29, 2007.

DESCRIPTION

The present invention relates to a process for producing water-absorbing polymeric particles by polymerizing a monomer solution or suspension comprising at least one unsaturated carboxylic acid and at least one hydroquinone monoether, and coating the polymeric particles with a salt of a tervalent metal cation of a carboxylic acid and/or a basic salt of a tervalent metal cation, the water-absorbable polymeric particles obtainable by the process and also the use of said polymeric particles in hygiene articles and packaging materials.

Water-absorbing polymers are in particular polymers of (co)polymerized hydrophilic monomers, graft (co)polymers of one or more hydrophilic monomers on a suitable grafting base, crosslinked ethers of cellulose or of starch, crosslinked carboxymethylcellulose, partially crosslinked polyalkylene oxide or natural products that are swellable in aqueous fluids, such as guar derivatives for example. Such polymers are used as products capable of absorbing aqueous solutions to manufacture diapers, tampons, sanitary napkins and other hygiene articles, but also as water-retaining agents in market gardening.

To improve their performance characteristics, such as for example Saline Flow Conductivity (SFC) in the diaper and Absorbency under Load (AUL0.7 psi), water-absorbing polymeric particles are generally postcrosslinked. This postcrosslinking can be carried out in the aqueous gel phase. But preferably ground and classified (base) polymeric particles are surface coated with a postcrosslinker, dried and thermally postcrosslinked. Useful crosslinkers for this purpose are compounds which comprise two or more groups capable of forming covalent bonds with the carboxylate groups of the water-absorbing polymer, or capable of linking together the at least two carboxyl groups or other functional groups of at least two different polymeric chains of the base polymer covalently or ionically.

Postcrosslinking is described in the monograph "Modern Superabsorbent Polymer Technology", F. L. Buchholz and A. T. Graham, Wiley-VCH, 1998, pages 97 to 103. Typically, the water-absorbing polymeric particles are coated with the postcrosslinker and thermally postcrosslinked by the polymeric particles being heated, and concurrently dried, by means of hot air or by means of contact drying.

WO 2006/015729 A2 describes a postcrosslinking process wherein mixtures of cyclic carbamates and diols are used.

WO 2000/053664 A1 describes the production of water-absorbing polymeric particles having high absorbency under load (AUL0.7 psi) and high saline flow conductivity (SFC) wherein the polymeric particles are postcrosslinked with an organic postcrosslinker and a uni- or multivalent metal cation.

Saline flow conductivity (SFC) can also be increased by coating with water-insoluble metal phosphates, for example calcium phosphate. Such a process is described in WO 2006/015729 A2 for example.

Ultrathin hygiene articles require water-absorbing polymeric particles of high whiteness. The production of such water-absorbing polymeric particles of high whiteness is described in particular in DE 10 2004 057 874 A1, expressly part of the present disclosure. With ultrathin diapers or feminine hygiene products, even minimal variations in color are visible through the thin topsheet, and are not accepted by customers. But even the use of superabsorbents in thicker hygiene articles often requires a very white product for customer acceptance reasons, since yellowing is often associated with a product being soiled or of low quality. Furthermore, when ordinary water-absorbing polymeric particles are stored, they may degrade in color to yellow and brown before being processed or after processing into the final hygiene article. This effect reduces the storability and marketability of the hygiene products and occurs particularly under unfavorable conditions of storage, as for example at elevated storage temperatures and high relative humidity. More particularly, hygiene articles thus produced can color degrade, and lead to complaints, even before retail sale or before use by the consumer. However, a conceivable separate package for each individual hygiene article is associated with high costs.

Nor may the water-absorbing polymeric particles give off unpleasant odors, especially when loaded with fluid during use of the hygiene article.

The present invention therefore has for its object to provide an improved process for producing water-absorbing polymeric particles which produces polymeric particles of a high whiteness which substantially persists even when the polymeric particles are stored under unfavorable atmospheric conditions for a prolonged period.

The present invention further has for its object to provide a process for producing water-absorbing polymeric particles which produces polymeric particles which are free of noticeable odors, especially when loaded with fluid.

The present invention further has for its object to provide water-absorbing polymeric particles of high whiteness for use in hygiene articles.

The present invention further has for its object to provide water-absorbing polymeric particles of high whiteness, high saline flow conductivity, high absorbency and good color stability after prolonged storage for use in ultrathin hygiene articles.

We have found that this object is achieved by a process for producing water-absorbing polymeric particles by polymerizing a monomer solution or suspension comprising a) at least one unsaturated carboxylic acid, which may be at least partially neutralized, and
b) at least one hydroquinone monoether and coating the polymeric particles with at least one salt of a tervalent metal cation wherein the salt of the tervalent metal cation is the salt of a carboxylic acid and/or a basic salt.

The degree of neutralization of the unsaturated carboxylic acid a) is preferably in the range from 25 to 95 mol %, more preferably in the range from 27 to 80 mol % and most preferably in the range from 27 to 30 mol % or from 40 to 75 mol %.

The level of hydroquinone monoether b) in the monomer solution is preferably in the range from 0.001% to 0.016% by weight, more preferably in the range from 0.003% to 0.013% by weight and most preferably in the range from 0.005% to 0.007% by weight, all based on the unsaturated carboxylic acid a). The preferred hydroquinone monoether is hydroquinone monomethyl ether.

The tervalent metal cation is preferably a metal cation of the third main group, the third transition group or of the lanthanide group of the periodic table, more preferably aluminum, scandium, yttrium, lanthanum or cerium and most preferably aluminum.

The salts of the tervalent metal cations are preferably salts of carboxylic acids and/or basic salts, such as acetates, propionates, tartrates, maleates, citrates, lactates and/or hydroxides, more preferably salts of 2-hydroxy carboxylic acids, such as citrates and/or lactates, and most preferably lactates.

Hydroxides of tervalent metal cations are in particular water-soluble and water-dispersible alkali metal and alkaline earth metal aluminates and their hydrates, preferably sodium aluminate and its hydrates.

Suitable salts of tervalent metal cations are for example aluminum acetate, aluminum propionate, aluminum citrate, aluminum lactate and sodium aluminate.

The amount of salt of the tervalent metal cation, based on the polymeric particles, is typically in the range from 0.001% to 5% by weight, preferably in the range from 0.01% to 2.5% by weight, more preferably in the range from 0.1% to 1.5% by weight, even more preferably in the range from 0.1% to 1% by weight and most preferably in the range from 0.4 to 0.7% by weight.

The salt of the tervalent metal cation can be used as a solution or suspension.

In a preferred embodiment of the present invention, the polymeric particles are coated with at least one basic salt of a bivalent metal cation.

Basic salts are salts capable of elevating the pH of an acidic aqueous solution, preferably of 0.1 N hydrochloric acid. Basic salts are typically salts of a strong base with a weak acid.

The bivalent metal cation is preferably a metal cation of the second main group of the periodic table, more preferably calcium and/or magnesium and most preferably calcium.

The salts of the bivalent metal cations are preferably salts of weak inorganic acids, weak organic acids and/or salts of amino acids, more preferably hydroxides, bicarbonates, carbonates, acetates, propionates, citrates, gluconates, lactates, tartrates, maleates and/or fumarates and most preferably hydroxides, bicarbonates, carbonates, propionates and/or lactates.

Useful salts of bivalent metal cations are for example calcium hydroxide, magnesium hydroxide, zinc oxide, calcium bicarbonate, magnesium bicarbonate, calcium acetate, magnesium acetate, calcium propionate, magnesium propionate, calcium carbonate and magnesium carbonate.

The amount of basic salt of the bivalent metal cation, based on the polymeric particles, is typically in the range from 0.001% to 5% by weight, preferably in the range from 0.01% to 2.5% by weight, more preferably in the range from 0.1% to 1.5% by weight, even more preferably in the range from 0.1% to 1% by weight and most preferably in the range from 0.4% to 0.7% by weight.

The basic salt of the bivalent metal cation can be used as a solution or suspension. Examples thereof are calcium lactate solutions or calcium hydroxide suspensions.

The salts used of the bi- and/or tervalent metal cation may comprise further, secondary constituents such as unneutralized carboxylic acid and/or alkali metal salts of neutralized carboxylic acid. Preferred alkali metal salts are those of sodium, of potassium and of ammonium. They are typically used as an aqueous solution obtained by dissolving the solid salts in water or preferably directly created as such, obviating drying and purifying steps, if appropriate.

In a particularly preferred embodiment of the present invention, the water-absorbing polymeric particles are thermally postcrosslinked.

In this process, the water-absorbing polymeric particles are preferably coated with the tervalent metal cation and/or if appropriate with the basic salt of the bivalent metal cation prior to thermal postcrosslinking.

The total partial pressure of one or more oxidizing gases in the atmosphere overlying the polymeric particles during thermal postcrosslinking is preferably less than 140 mbar, more preferably less than 100 mbar, even more preferably less than 50 mbar and most preferably less than 10 mbar.

Oxidizing gases are entities which have a vapor pressure of not less than 1013 mbar at 23° C. and act as oxidizing agents in combustion processes. examples being oxygen, nitrous oxide and nitric oxide, especially oxygen.

The oxygen partial pressure during thermal postcrosslinking in the atmosphere overlying the water-absorbing polymeric particles is preferably less than 140 mbar, more preferably less than 100 mbar, even more preferably less than 50 mbar and most preferably less than 10 mbar.

When thermal postcrosslinking is carried out at ambient pressure, i.e., at a total pressure of around 1013 mbar, the total partial pressure of the oxidizing gases is defined via their volume fraction. The fraction of the oxidizing gases is preferably less than 14% by volume, more preferably less than 10% by volume, even more preferably less than 5% by volume and most preferably less than 1% by volume.

Thermal postcrosslinking is preferably carried out at reduced pressure, i.e., at a total pressure of less than 1013 mbar. The total pressure is for example less than 670 mbar, preferably less than 480 mbar, more preferably less than 300 mbar and most preferably less than 200 mbar. When drying and postcrosslinking are carried out under air having an oxygen content of 20.8% by volume, the oxygen partial pressures corresponding to the abovementioned total pressures are 139 mbar (670 mbar), 100 mbar (480 mbar), 62 mbar (300 mbar) and 42 mbar (200 mbar), the respective total pressures being in the parentheses.

Coarse polymeric particles are advantageously removed before thermal postcrosslinking. For example by means of a sieve having a mesh size of preferably 700 µm or less, more preferably 650 µm or less and most preferably 600 µm or less.

Preferred postcrosslinkers are 1,3-diols, such as 1,3-propanediol, 1,3-butanediol and 2-methyl-1,3-propanediol, and/or cyclic carbamates, such as 2-oxazolidone and N-(2-hydroxyethyl)-2-oxazolidone.

The use of monomer solutions comprising both hydroquinone monomethyl ether and sodium peroxodisulfate gives water-absorbing polymeric particles very prone to color degrade. One way to produce white water-absorbing polymer particles was therefore to remove hydroquinone monomethyl ether before polymerization. But it was also possible to replace sodium peroxodisulfate by other polymerization initiators.

The present invention rests on the discovery that salts of a strong acid, such as aluminum sulfate, can lead to color degradation in the event of storage under unfavorable climatic conditions. The inventors found that salts of weak acids do not have this undesirable property.

Moreover, this color degradation can be prevented by coating the polymer particles with basic salts of bivalent metal cations.

Long-term stability to color degradation can be further enhanced by removing comparatively large polymeric particles prior to thermal postcrosslinking.

Furthermore, using tervalent metal salts of weak acids instead of aluminum sulfate gives water-absorbing polymeric particles having an improved performance portfolio, i.e., higher saline flow conductivity (SFC) and higher absorbency under load (AUL0.7 psi).

The crosslinked, water-absorbing polymeric particles are described for example in the monograph "Modern Superabsorbent Polymer Technology", F. L. Buchholz and A. T. Graham, Wiley-VCH, 1998, or in Ullmann's Encyclopedia of Industrial Chemistry, 6th edition, volume 35, pages 73 to 103.

The water-absorbing polymeric particles are obtained by polymerizing a monomer solution or suspension comprising
a) at least one unsaturated carboxylic acid,
b) at least one hydroquinone monoether,
c) optionally one or more inorganic peroxides,
d) optionally one or more crosslinkers,
e) optionally one or more ethylenically and/or allylically unsaturated monomers copolymerizable with a), and
f) optionally one or more water-soluble polymers onto which the monomers a), d) and e) can be at least partly grafted.

Useful unsaturated carboxylic acids a) include for example ethylenically unsaturated carboxylic acids, such as acrylic acid, methacrylic acid, maleic acid, fumaric acid and itaconic acid. Acrylic acid and methacrylic acid are particularly preferred unsaturated carboxylic acids a). Acrylic acid is very particularly preferred.

Hydroquinone monoethers b) are hydroquinones etherified at exactly one hydroxyl group. Useful hydroquinone monoethers b) include hydroquinone monoalkoxy ethers such as hydroquinone monomethyl ether and hydroquinone monoethyl ether, preferably hydroquinone monomethyl ether, and/or tocopherols, such as alpha-tocopherol, racemic alpha-tocopherol and RRR-alpha-tocopherol, preferably racemic alpha-tocopherol and RRR-alpha-tocopherol.

The monomer solution comprises preferably not more than 0.016% by weight, more preferably not more than 0.013% by weight, most preferably not more than 0.007% by weight, preferably at least 0.001% by weight, more preferably at least 0.003% by weight and most preferably at least 0.005% by weight of hydroquinone monoether all based on unsaturated carboxylic acid a), with unsaturated carboxylic acid salts being arithmetically counted as unsaturated carboxylic acid a). For example, the monomer solution can be produced using an acrylic acid having an appropriate hydroquinone monoether content.

The inorganic peroxide c) is for example hydrogen peroxide, a persulfate, such as sodium peroxodisulfate, and/or a perphosphate, such as sodium peroxodiphosphate, preferably a salt, more preferably a persulfate or a perphosphate, most preferably a persulfate, for example sodium peroxodisulfate.

The process of the present invention preferably utilizes an initiator system comprising peroxodisulfate and/or peroxodiphosphate.

The process of the present invention preferably initiates the reaction using an initiator system comprising peroxodisulfate, for example sodium peroxodisulfate, potassium peroxodisulfate and/or ammonium peroxodisulfate, ascorbic acid and hydrogen peroxide. The two components ascorbic acid and hydrogen peroxide can be replaced or supplemented by any other initiator known to one skilled in the art. Such substitutes comprise other reducing and oxidizing agents and also the known azo and photo initiators as well as catalytically active metal cations such as iron cations for example.

The water-absorbing polymers are preferably in a crosslinked state, i.e., the addition polymerization is carried out in the presence of compounds having two or more polymerizable groups which can be free-radically interpolymerized into the polymer network. Useful crosslinkers d) include for example ethylene glycol dimethacrylate, diethylene glycol diacrylate, allyl methacrylate, trimethylolpropane triacrylate, triallylamine, tetraallyloxyethane as described in EP 0 530 438 A1, di- and triacrylates as described in EP 0 547 847 A1, EP 0 559 476 A1, EP 0 632 068 A1, WO 93/21237 A1, WO 2003/104299 A1, WO 2003/104300 A1, WO 2003/104301 A1 and in DE 103 31 450 A1, mixed acrylates which, as well as acrylate groups, comprise further ethylenically unsaturated groups, as described in DE 103 31 456 A1 and 103 55 401 A1, or crosslinker mixtures as described for example in DE 195 43 368 A1, DE 196 46 484 A1, WO 90/15830 A1 and WO 2002/32962 A2.

Useful crosslinkers d) include in particular N,N'-methylenebisacrylamide and N,N'-methylenebismethacrylamide, esters of unsaturated mono- or polycarboxylic acids of polyols, such as diacrylate or triacrylate, for example butanediol diacrylate, butanediol dimethacrylate, ethylene glycol diacrylate, ethylene glycol dimethacrylate and also trimethylolpropane triacrylate and allyl compounds, such as allyl (meth)acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described for example in EP 0 343 427 A2. Useful crosslinkers d) further include pentaerythritol diallyl ether, pentaerythritol triallyl ether, pentaerythritol tetraallyl ether, polyethylene glycol diallyl ether, ethylene glycol diallyl ether, glycerol diallyl ether, glycerol triallyl ether, polyallyl ethers based on sorbitol, and also ethoxylated variants thereof. The process of the present invention may utilize di(meth)acrylates of polyethylene glycols, the polyethylene glycol used having a molecular weight between 300 and 1000.

However, particularly advantageous crosslinkers d) are di- and triacrylates of 3- to 20-tuply ethoxylated glycerol, of 3- to 20-tuply ethoxylated trimethylolpropane, of 3- to 20-tuply ethoxylated trimethylolethane, especially di- and triacrylates of 2- to 6-tuply ethoxylated glycerol or of 2- to 6-tuply ethoxylated trimethylolpropane, of 3-tuply propoxylated glycerol, of 3-tuply propoxylated trimethylolpropane, and also of 3-tuply mixedly ethoxylated or propoxylated glycerol, of 3-tuply mixedly ethoxylated or propoxylated trimethylolpropane, of 15-tuply ethoxylated glycerol, of 15-tuply ethoxylated trimethylolpropane, of at least 40-tuply ethoxylated glycerol, of at least 40-tuply ethoxylated trimethylolethane and also of at least 40-tuply ethoxylated trimethylolpropane.

Very particularly preferred for use as crosslinkers d) are diacrylated, dimethacrylated, triacrylated or trimethacrylated multiply ethoxylated and/or propoxylated glycerols as described for example in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. The triacrylates of 3- to 5-tuply ethoxylated and/or propoxylated glycerol are most preferred. These are notable for particularly low residual levels (typically below 0.0010% by weight) in the water-absorbing polymeric particles and the aqueous extracts of water-absorbing polymeric particles produced therewith have an almost unchanged surface tension (typically not less than 0.068 N/m) compared with water at the same temperature.

Examples of ethylenically unsaturated monomers e) which are copolymerizable with the unsaturated carboxylic acids a) are acrylamide, methacrylamide, crotonamide, dimethylaminoethyl methacrylate, dimethylaminoethyl acrylate, dimethylaminopropyl acrylate, diethylaminopropyl acrylate, dimethylaminobutyl acrylate, dimethylaminoethyl methacrylate, diethylaminoethyl methacrylate, dimethylaminoneopentyl acrylate and dimethylaminoneopentyl methacrylate.

Useful water-soluble polymers f) include polyvinyl alcohol, polyvinylpyrrolidone, starch, starch derivatives, polyglycols or polyacrylic acids, preferably polyvinyl alcohol and starch.

The preparation of a suitable base polymer and also further useful hydrophilic ethylenically unsaturated carboxylic acids a) are described in DE 199 41 423 A1, EP 0 686 650 A1, WO 2001/45758 A1 and WO 2003/14300 A1.

The reaction is preferably carried out in a kneader as described for example in WO 2001/38402 A1, or on a belt reactor as described for example in EP 0 955 086 A2.

The acid groups of the hydrogels obtained are typically in a partially neutralized state, the extent of neutralization preferably being in the range from 25 to 95 mol %, more preferably in the range from 27 to 80 mol % and even more preferably in the range from 27 to 30 mol % or from 40 to 75 mol %, for which the customary neutralizing agents can be used, for example alkali metal hydroxides, alkali metal oxides, alkali metal carbonates or alkali metal bicarbonates and also mixtures thereof. Optionally or in admixture with the alkali metal compounds mentioned, the corresponding alkaline earth metal compounds and here preferably the compounds of magnesium and calcium can also, be used for the neutralization. Ammonium salts can also be used instead of alkali metal salts. Sodium and potassium are particularly preferred as alkali metals, but most preference is given to sodium hydroxide, sodium carbonate or sodium bicarbonate and also mixtures thereof. Typically, neutralization is achieved by admixing the neutralizing agent as an aqueous solution, as a melt or else preferably as a solid material. For example, sodium hydroxide having a water fraction of distinctly below 50% by weight can be present as a waxy mass having a melting point above 23° C. In this case, metering as piece goods or melt at elevated temperature is possible.

Neutralization can be carried out after polymerization, at the hydrogel stage. But it is also possible to neutralize up to 40 mol %, preferably from 10 to 30 mol % and more preferably from 15 to 25 mol % of the acid groups before polymerization by adding a portion of the neutralizing agent to the monomer solution and setting the desired final degree of neutralization only after polymerization, at the hydrogel stage. The monomer solution may be neutralized by admixing the neutralizing agent. The hydrogel can be mechanically comminuted, for example by means of a meat grinder, in which case the neutralizing agent can be sprayed, sprinkled or poured on and then carefully mixed in. To this end, the gel mass obtained can be repeatedly minced for homogenization. Neutralization of the monomer solution directly to the final degree of neutralization is preferred.

In a particularly preferred embodiment of the invention, the degree of neutralization is set to 65-72 mol % by means of 50% by weight aqueous sodium hydroxide solution of membrane grade.

The neutralized hydrogel is then dried with a belt or drum dryer until the residual moisture content is preferably below 15% by weight and especially below 10% by weight, the water content being determined by EDANA (European Disposables and Nonwovens Association) recommended test method No. WSP 230.2-05 "Moisture content". Selectively, drying can also be carried out using a fluidized bed dryer or a heated plowshare mixer. To obtain particularly white products, it is advantageous to dry this gel by ensuring rapid removal of the evaporating water. To this end, the dryer temperature must be optimized, the air feed and removal has to be policed, and at all times sufficient venting must be ensured. Drying is naturally all the more simple—and the product all the more white—when the solids content of the gel is as high as possible. The solids content of the gel prior to drying is therefore preferably between 30% and 80% by weight. It is particularly advantageous to vent the dryer with nitrogen or some other non-oxidizing inert gas. Selectively, however, simply just the partial pressure of the oxygen can be lowered during drying to prevent oxidative yellowing processes. But in general adequate venting and removal of the water vapor will likewise still lead to an acceptable product. A very short drying time is generally advantageous with regard to color and product quality.

A further important function of drying the gel is the ongoing reduction in the residual monomer content of the polymeric particles. This is because any residual initiator will decompose during drying, leading to any residual monomers becoming interpolymerized. In addition, the evaporating amounts of water will entrain any free water-vapor-volatile monomers still present, such as acrylic acid for example, and thus likewise lower the residual monomer content of the polymeric particles.

The dried hydrogel is then ground and sieved, useful grinding apparatus typically including single or multiple stage roll mills, preferably two or three stage roll mills, pin mills, hammer mills or swing mills.

The particle sizes of the ground polymeric particles of the dried hydrogel after classification by passing them through sieves is typically in the range from 0 to 1000 µm, preferably in the range from 150 to 850 µm, more preferably in the range from 200 to 800 µm and most preferably in the range from 200 to 700 µm.

It is preferable for less than 2% by weight, more preferably less than 1.5% by weight and most preferably less than 1% by weight of the polymeric particles to have a particle size of above 850 µm.

It is preferable for less than 5% by weight, more preferably less than 3% by weight, even more preferably less than 1% by weight and most preferably less than 0.3% by weight of the polymeric particles to have a particle size of below 150 µm.

It is preferable for at least 90% by weight, more preferably at least 95% by weight, even more preferably at least 98% by weight and most preferably at least 99% by weight of the polymeric particles to have a particle size in the range from 150 to 850 µm.

In a preferred embodiment at least 90% by weight, more preferably at least 95% by weight, even more preferably at least 98% by weight and most preferably at least 99% by weight of the polymeric particles have a particle size in the range from 150 to 700 µm.

In a more preferred embodiment at least 90% by weight, more preferably at least 95% by weight, even more preferably at least 98% by weight and most preferably at least 99% by weight of the polymeric particles have a particle size in the range from 150 to 600 µm.

In a even more preferred embodiment at least 85% by weight, more preferably at least 90% by weight, even more preferably at least 98% by weight and most preferably at least 99% by weight of the polymeric particles have a particle size in the range from 200 to 500 µm.

The process of the present invention is also an advantageous way to produce spherical particles by suspension, spray or droplet polymerization processes. Of particular suitability are particles having a narrow particle distribution and also irregular particles formed by agglomeration of spherical particles. The process of the present invention also provides a way to produce irregular particles or regular nonspherical particles from such polymerizations.

In one embodiment of the process according to the present invention, the base polymer is coated with at least one salt of a tervalent metal cation of a carboxylic acid and/or at least one basic salt of a bivalent metal cation. The salt of the tervalent metal cation is preferably soluble in water.

Preferably, the water-absorbing polymeric particles are sprayed with an aqueous solution comprising aluminum cations.

In a further preferred embodiment of the process according to the present invention, the base polymer is coated with at least one tervalent metal cation selected from the water-soluble salts of the elements of the third main group, the third transition group or the lanthanide group of the periodic table, preferably aluminum, scandium, yttrium, lanthanum and/or cerium, and at least one basic salt of a bivalent metal cation.

In a very particularly preferred embodiment of the process according to the present invention, the base polymer is coated with at least one water-soluble salt of aluminum and with at least one water-soluble basic salt of calcium.

Preferably, the water-absorbing polymeric particles are sprayed with an aqueous solution comprising aluminum cations and calcium and/or magnesium cations.

Water-soluble salts for the purposes of the present invention are salts of bi- and tervalent metal cations that have a solubility in water at 20° C. of at least 0.5 g of salt per liter of water, preferably at least 1 g of salt per l of water, more preferably at least 10 g of salt per l of water, even more preferably at least 100 g of salt per l of water and most preferably at least 200 g of salt per l of water. Also useful for the purposes of the present invention are such salts which have this minimum solubility at the spraying temperature of the spray solution.

When this water solubility is not sufficient for preparing a spray solution of the desired concentration, dispersions of the solid salt in its saturated aqueous solution can also be used.

When the solution of the tervalent metal cation is not miscible with the solution of the bivalent metal cation without precipitation occurring, the solutions can be spray dispensed separately in succession or concurrently from two nozzles.

Particular preference is given to such salts of which the aqueous solutions, comprising the tervalent metal cation and the bivalent metal cation, are miscible in any proportion.

Useful salts for the purposes of the present invention of ter- and bivalent metal cations preferably comprise anions derived from weak inorganic acids or weak organic carboxylic acids or amino acids. The underlying acids of the anions in the salts of the present invention are either volatile as for example carbonic acid, sulfurous acid, water or acetic acid, or thermally decomposable such as for example lactic acid or tartaric acid, and they can also be thermally stable under the drying conditions.

Examples of what is suitable in the process of the present invention are aluminum acetate, aluminum lactate, aluminum propionate, aluminum citrate, sodium aluminate, acid-soluble aluminum hydroxide, calcium hydroxide, calcium bicarbonate, calcium acetate, calcium propionate, calcium citrate, calcium gluconate, calcium lactate, calcium tartrate, calcium maleate and calcium fumarate. The corresponding salts with other metal cations according to the present invention can likewise be used.

Particular preference in the process of the present invention is given to aluminum lactate, calcium hydroxide, calcium bicarbonate, calcium propionate and calcium lactate.

It is also advantageous to use the hydrates of the above-mentioned salts. The hydrates, for example the pentahydrate of aluminum lactate, are quicker to dissolve in water than the anhydrous salts.

Typically, the salts are spray dispensed with a water quantity of not more than 15% by weight, preferably not more than 8% by weight, more preferably not more than 5% by weight and most preferably not more than 2% by weight, based on the polymeric particles used. The process of the present invention advantageously utilizes water-soluble salts.

In a further particular embodiment, however, it is also possible to spray the polymeric particles with a salt of a tervalent metal cation together with finely water-dispersed calcium carbonate. The salt of the tervalent metal cation is preferably water soluble and is preferably an aluminum salt, more preferably aluminum lactate. In this case, the calcium carbonate has particle sizes of preferably less than 50 µm, more preferably less than 30 µm, even more preferably less than 10 µm and most preferably in the range from 0.01 to 5 µm.

The base polymers are preferably postcrosslinked. Useful postcrosslinkers are compounds comprising two or more groups capable of forming covalent bonds with the carboxylate groups of the polymers. Useful compounds are for example alkoxysilyl compounds, polyaziridines, polyamines, polyamidoamines, di- or polyglycidyl compounds as described in EP 0 083 022 A2, EP 0 543 303 A1 and EP 0 937 736 A2, polyhydric alcohols as described in DE 33 14 019 A1, DE 35 23 617 A1 and EP 0 450 922 A2, or 1-hydroxyalkylamides as described in DE 102 04 938 A1 and U.S. Pat. No. 6,239,230. It is also possible to use compounds of mixed functionality, such as glycidol, 3-ethyl-3-oxetanemethanol (trimethylolpropaneoxetane), as described in EP 1 199 327 A2, aminoethanol, diethanolamine, triethanolamine or compounds which develop a further functionality after the first reaction, such as ethylene oxide, propylene oxide, isobutylene oxide, aziridine, azetidine or oxetane.

Useful postcrosslinkers are further said to include by DE 40 20 780 C1 cyclic carbonates, by DE 198 07 502 A1 2-oxazolidone and its derivatives, such as N-(2-hydroxyethyl)-2-oxazolidone, by DE 198 07 992 C1 bis- and poly-2-oxazolidones, by DE 198 54 573 A1 2-oxotetrahydro-1,3-oxazine and its derivatives, by DE 198 54 574 A1 N-acyl-2-oxazolidones, by DE 102 04 937 A1 cyclic ureas, by DE 103 34 584 A1 bicyclic amide acetals, by EP 1 199 327 A2 oxetanes and cyclic ureas and by WO 2003/031482 A1 morpholine-2,3-dione and its derivatives.

Postcrosslinking is typically carried out by spraying a solution of the postcrosslinker onto the hydrogel or the dry base-polymeric particles. Spraying is followed by thermal drying, and the postcrosslinking reaction can take place not only before but also during drying.

The solution comprising the at least one tervalent metal cation can be separately metered and spray dispensed before, during or after postcrosslinking, or be directly added to the postcrosslinker solution. Preferably, the at least one tervalent metal cation is simply added directly to the postcrosslinker solution. When the at least one tervalent metal cation is applied separately before or after postcrosslinking, any coating apparatus known to one skilled in the art and any mixer can be used.

The solution comprising the at least one tervalent metal cation and the at least one bivalent metal cation can be separately metered and spray dispensed before, during or after postcrosslinking or be added directly to the postcrosslinker solution. Preferably, the ter- and bivalent metal cations are simply added directly to the postcrosslinker solution. When the solution comprising the at least one tervalent metal cation and the at least one bivalent metal cation is applied separately before or after postcrosslinking, any coating apparatus known to one skilled in the art and any mixer can be used. The two metal cations, preferably aluminum and calcium cations, can also be metered from separate solutions concurrently, with their metering times overlapping, or with successive metering periods.

Particular preference is given to such salts of which the aqueous solutions comprising the tervalent metal cation and the bivalent metal cation are miscible in any proportion. Very particular preference is given to mixtures of such solutions that are directly miscible with the postcrosslinking solution without precipitation occurring in the process.

Preferably, the water-soluble salts are directly dissolved in the aqueous postcrosslinker solution, if appropriate by addition of water, or the water-soluble salts are dissolved in water or, if appropriate, dispersed in their saturated solution.

Preferred postcrosslinkers are amide acetals or carbamates of the general formula (I)

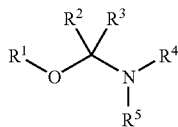

(I)

where
$R^1$ is $C_1$-$C_{12}$-alkyl, $C_2$-$C_{12}$-hydroxyalkyl, $C_2$-$C_{12}$-alkenyl or $C_6$-$C_{12}$-aryl,
$R^2$ is X or $OR^6$
$R^3$ is hydrogen, $C_1$-$C_{12}$-alkyl, $C_2$-$C_{12}$-hydroxyalkyl, $C_2$-$C_{12}$-alkenyl or $C_6$-$C_{12}$-aryl, or X,
$R^4$ is $C_1$-$C_{12}$-alkyl, $C_2$-$C_{12}$-hydroxyalkyl, $C_2$-$C_{12}$-alkenyl or $C_6$-$C_{12}$-aryl
$R^5$ is hydrogen, $C_1$-$C_{12}$-alkyl, $C_2$-$C_{12}$-hydroxyalkyl, $C_2$—$CO_2$-alkenyl, $C_1$-$C_{12}$-acyl or $C_6$-$C_{12}$-aryl,
$R^6$ is $C_1$-$C_{12}$-alkyl, $C_2$-$C_{12}$-hydroxyalkyl, $C_2$-$C_{12}$-alkenyl or $C_6$-$C_{12}$-aryl and
X is a carbonyl oxygen common to $R^2$ and $R^3$,
wherein $R^1$ and $R^4$ and/or $R^5$ and $R^6$ can be a bridged $C_2$-$C_6$-alkanediyl and wherein the abovementioned radicals $R^1$ to $R^6$ can still have in total one to two free valences and can be attached through these free valences to at least one suitable basic structure,
or polyhydric alcohols, in which case the molecular weight of the polyhydric alcohol is preferably less than 100 g/mol, preferably less than 90 g/mol, more preferably less than 80 g/mol and most preferably less than 70 g/mol per hydroxyl group and the polyhydric alcohol has no vicinal, geminal, secondary or tertiary hydroxyl groups, and polyhydric alcohols are either diols of the general formula (IIa)

HO—$R^6$—OH (IIa)

where $R^6$ is either an unbranched dialkyl radical of the formula —$(CH_2)_n$—, where n is an integer from 3 to 20 and preferably from 3 to 12, and both the hydroxyl groups are terminal, or an unbranched, branched or cyclic dialkyl radical or polyols of the general formula (IIb)

(IIb)

where $R^7$, $R^8$, $R^9$ and $R^{10}$ are independently hydrogen, hydroxyl, hydroxymethyl, hydroxyethyloxymethyl, 1-hydroxyprop-2-yloxymethyl, 2-hydroxypropyloxymethyl, methyl, ethyl, n-propyl, isopropyl, n-butyl, n-pentyl, n-hexyl, 1,2-dihydroxyethyl, 2-hydroxyethyl, 3-hydroxypropyl or 4-hydroxybutyl and in total 2, 3 or 4 and preferably 2 or 3 hydroxyl groups are present, and not more than one of $R^7$, $R^8$, $R^9$ and $R^{10}$ is hydroxyl,
or cyclic carbonates of the general formula (III)

(III)

where $R^{11}$, $R^{12}$, $R^{13}$, $R^{14}$, $R^{15}$ and $R^{16}$ are independently hydrogen, methyl, ethyl, n-propyl, isopropyl, n-butyl, sec-butyl or isobutyl, and n is either 0 or 1,
or bisoxazolines of the general formula (IV)

(IV)

where $R^{17}$, $R^{18}$, $R^{19}$, $R^{20}$, $R^{21}$, $R^{22}$, $R^{23}$ and $R^{24}$ are independently hydrogen, methyl, ethyl, n-propyl, isopropyl, n-butyl, sec-butyl or isobutyl and $R^{25}$ is a single bond, a linear, branched or cyclic $C_2$-$C_{12}$-dialkyl radical or a polyalkoxydiyl radical which is constructed of one to ten ethylene oxide and/or propylene oxide units, as possessed by polyglycol dicarboxylic acids for example.

Preferred postcrosslinkers are extremely selective. By producing and secondary reactions which lead to volatile and hence malodorous compounds are minimized. The water-absorbing polymers produced with preferred postcrosslinkers are therefore odor neutral even in the moistened state.

Epoxy compounds, by contrast, may at high temperatures in the presence of suitable catalysts undergo various rearrangement reactions which lead to aldehydes or ketones for example. These can then undergo further secondary reactions which eventually lead to the formation of malodorous impurities which are undesirable in hygiene articles on account of their odor. Therefore, epoxy compounds are less suitable for postcrosslinking above a temperature of about 140 to 150° C. Amino- or imino-comprising postcrosslinkers will at similar temperatures undergo even more involved rearrangement reactions which tend to give rise to malodorous trace impurities and brownish product discolorations.

Polyhydric alcohols employed as postcrosslinkers require high postcrosslinking temperatures on account of their low reactivity. Alcohols comprising vicinal, geminal, secondary and tertiary hydroxyl groups give rise to byproducts which are undesirable in the hygiene sector because they lead to unpleasant odors and/or discolorations of the corresponding hygiene article during manufacture or use.

Preferred postcrosslinkers of the general formula (I) are 2-oxazolidones, such as 2-oxazolidone and N-(2-hydroxyethyl)-2-oxazolidone, N-methyl-2-oxazolidone, N-acyl-2-oxazolidones, such as N-acetyl-2-oxazolidone, 2-oxotetrahydro-1,3-oxazine, bicyclic amide acetals, such as 5-methyl-1-aza-4,6-dioxabicyclo[3.3.0]octane, 1-aza-4,6-dioxabicyclo[3.3.0]octane and 5-isopropyl-1-aza-4,6-dioxabicyclo[3.3.0]octane, bis-2-oxazolidones and poly-2-oxazolidones.

Particularly preferred postcrosslinkers of the general formula (I) are 2-oxazolidone, N-methyl-2-oxazolidone, N-(2-hydroxyethyl)-2-oxazolidone and N-(2-hydroxypropyl)-2-oxazolidone.

Preferred postcrosslinkers of the general formula (IIa) are 1,3-propanediol, 1,5-pentanediol, 1,6-hexanediol and 1,7-heptanediol. Further examples of postcrosslinkers of the formula (IIa) are 1,3-butanediol, 1,8-octanediol, 1,9-nonanediol and 1,10-decanediol.

The diols are preferably soluble in water in that the diols of the general formula (IIa) dissolve in water at 23° C. to an extent of not less than 30% by weight, preferably not less than 40% by weight, more preferably not less than 50% by weight and most preferably not less than 60% by weight, examples being 1,3-propanediol and 1,7-heptanediol. Even more preference is given to such postcrosslinkers as are liquid at 25° C.

Preferred postcrosslinkers of the general formula (IIb) are 1,2,3-butanetriol, 1,2,4-butanetriol, glycerol, trimethylolpropane, trimethylolethane, pentaerythritol, ethoxylated glycerol, trimethylolethane or trimethylolpropane each having 1 to 3 ethylene oxide units per molecule and propoxylated glycerol, trimethylolethane or trimethylolpropane each having 1 to 3 propylene oxide units per molecule. Preference is further given to 2-tuply ethoxylated or propoxylated neopentylglycol. Particular preference is given to 2-tuply and 3-tuply ethoxylated glycerol, neopentylglycol, 2-methyl-1,3-propanediol and trimethylolpropane.

Preferred polyhydric alcohols (IIa) and (IIb) have a 23° C. viscosity of less than 3000 mPas, preferably less than 1500 mPas, more preferably less than 1000 mPas, even more preferably less than 500 mPas and most preferably less than 300 mPas.

Particularly preferred postcrosslinkers of the general formula (III) are ethylene carbonate and propylene carbonate.

A particularly preferred postcrosslinker of the general formula (IV) is 2,2'-bis(2-oxazoline).

The postcrosslinker is typically used in an amount of not more than 0.30% by weight, preferably not more than 0.15% by weight and more preferably in the range from 0.001% to 0.095% by weight, all percentages being based on the base polymer, as an aqueous solution.

It is possible to use a single postcrosslinker from the above selection or any desired mixtures of various postcrosslinkers.

The aqueous postcrosslinker solution, as well as the at least one postcrosslinker, can typically further comprise a cosolvent.

Cosolvents which are technically highly useful are $C_1$-$C_6$-alcohols, such as methanol, ethanol, n-propanol, isopropanol, n-butanol, sec-butanol, tert-butanol or 2-methyl-1-propanol, $C_2$-$C_5$-diols, such as ethylene glycol, 1,2-propylene glycol or 1,4-butane-diol, ketones, such as acetone, or carboxylic esters, such as ethyl acetate. The disadvantage with many of these cosolvents is that they have characteristic intrinsic odors.

The cosolvent itself is ideally not a postcrosslinker under the reaction conditions. However, in a borderline case and depending on the residence time and the temperature, the cosolvent may to some extent contribute to crosslinking. This will be the case in particular when the postcrosslinker is relatively inert and therefore is itself also able to form its cosolvent, as with the use for example of cyclic carbonates of the general formula (III), diols of the general formula (IIa) or polyols of the general formula (IIb). Such postcrosslinkers can also be used as cosolvent when admixed with more reactive postcrosslinkers, since the actual postcrosslinking reaction can then be carried out at lower temperatures and/or shorter residence times than in the absence of the more reactive crosslinker. Since the cosolvent is used in relatively large amounts and will also remain to some extent in the product, it must not be toxic.

The diols of the general formula (IIa), the polyols of the general formula (IIb) and also the cyclic carbonates of the general formula (III) are also useful as cosolvents in the process of the present invention. They perform this function in the presence of a reactive postcrosslinker of the general formula (I) and/or (IV) and/or of a di- or triglycidyl compound. However, preferred cosolvents in the process of the present invention are in particular the diols of the general formula (IIa), especially when the hydroxyl groups are sterically hindered by neighboring groups from participating in a reaction. Such diols are in principle also useful as postcrosslinkers, but for this require distinctly higher reaction temperatures or if appropriate higher use levels than sterically unhindered diols.

Particularly preferred cosolvents in the process of the present invention further include the polyols of the general formula (IIb). Among these, the 2- to 3-tuply alkoxylated polyols are preferred in particular. But particularly useful cosolvents further include 3- to 15-tuply and most particularly 5- to 10-tuply ethoxylated polyols based on glycerol, trimethylolpropane, trimethylolethane or pentaerythritol. 7-tuply ethoxylated trimethylolpropane is particularly useful.

Suitable sterically hindered and hence reaction-inert polyhydric alcohols further include polyhydric alcohols of no particular molecular weight which are free of vicinal, geminal or secondary hydroxyl groups.

Examples of such sterically hindered diols of the general formula (IIa) which are therefore particularly preferred for use as a cosolvent are 2,2-dimethyl-1,3-propanediol (neopentyl glycol), 2-methyl-1,3-propanediol and 2,4-dimethylpentane-2,4-diol.

Useful cosolvents further include di(trimethylolpropane) and also 5-ethyl-1,3-dioxane-5-methanol.

Particularly preferred combinations of less reactive postcrosslinker as cosolvent and reactive postcrosslinker are combinations of preferred polyhydric alcohols, diols of the general formula (IIa) and polyols of the general formula (IIb), with amide acetals or carbamates of the general formula (I).

Suitable combinations are for example 2-oxalolidone/1,2-propanediol and N-(2-hydroxyethyl)-2-oxazolidine/1,2-propanediol and ethylene glycol diglycidyl ether/1,2-propanediol.

Very particularly preferred combinations are 2-oxazolidone/1,3-propanediol and N-(2-hydroxyethyl)-2-oxazolidone/1,3-propanediol.

Further preferred combinations are those with ethylene glycol diglycidyl ether or glycerol diglycidyl or triglycidyl ether with the following solvents, cosolvents or cocrosslinkers: isopropanol, 1,3-propanediol, 2-methyl-1,3-propanediol, neopentyl glycol, 1,5-pentanediol, 1,6-hexanediol, 1,7-heptanediol or mixtures thereof.

The boiling point of the cosolvent is preferably no higher than 160° C., more preferably no higher than 140° C. and most preferably no higher than 120° C. or preferably no lower than 200° C., more preferably no lower than 220° C. and most preferably no lower than 250° C.

Particularly useful cosolvents in the process of the present invention therefore also include those which form a low boiling azeotrope with water or with a second cosolvent. The boiling point of this azeotrope is preferably no higher than 160° C., more preferably no higher than 140° C. and most preferably no higher than 120° C. Water vapor volatile cosolvents are likewise very useful, since they can be wholly or partly removed with the water evaporating in the course of drying.

Postcrosslinkers and cosolvents having a boiling point which is not distinctly above or below the temperature in the postcrosslinking dryer often lead surprisingly to water-absorbing polymeric particles having an undesirable chemical odor and the polymers are severely yellowed and often comprise black specks and other impurities.

The concentration of cosolvent in the aqueous postcrosslinker solution is frequently in the range from 15% to 50% by weight, preferably in the range from 15% to 40% by weight and more preferably in the range from 20% to 35% by weight, based on the postcrosslinker solution. In the case of cosolvents having a but limited miscibility with water, it will be advantageous to adjust the aqueous postcrosslinker solution such that there is only one phase, if appropriate by lowering the concentration of cosolvent.

A preferred embodiment does not utilize any cosolvent. The postcrosslinker is then only employed as a solution in water, with or without an added deagglomerating assistant.

The concentration of the at least one postcrosslinker in the aqueous postcrosslinker solution is for example in the range from 1% to 20% by weight, preferably in the range from 1.5% to 10% by weight and more preferably in the range from 2% to 5% by weight, based on the postcrosslinker solution.

The total amount of postcrosslinker solution based on base polymer is usually in the range from 0.3% to 15% by weight and preferably in the range from 2% to 6% by weight.

In a preferred embodiment, the base polymer is admixed with a surfactant deagglomerating assistant, for example a sorbitan monoester, such as sorbitan mono-cocoate and sorbitan monolaurate, or ethoxylated variants thereof, such as for example Polysorbat 20®. Very useful deagglomerating assistants further include the ethoxylated and alkoxylated derivatives of 2-propylheptanol, which are marketed by BASF AG of Germany under the brandnames of Lutensol XL® and Lutensol XP®.

Any anionic, cationic, nonionic or amphoteric surfactant is useful as a deagglomerating assistant, but preference for skin compatibility reasons is given to nonionic and amphoteric surfactants. The surfactant may also comprise nitrogen.

The deagglomerating assistant can be added separately or to the postcrosslinker solution. Preferably the deagglomerating assistant is added to the postcrosslinker solution.

The use level of deagglomerating assistant based on base polymer is for example in the range from 0% to 0.1% by weight, preferably in the range from 0% to 0.01% by weight and more preferably in the range from 0% to 0.002% by weight. The deagglomerating assistant is preferably dosed such that the surface tension of an aqueous extract of the swollen base polymer and/or of the swollen postcrosslinked water-absorbing polymer is not less than 0.060 N/m, preferably not less than 0.062 N/m and more preferably not less than 0.065 N/m and advantageously not more than 0.072 N/m, at 23° C.

The dried base polymer used in the process of the present invention typically has a residual moisture content in the range from 0% to 13% by weight and preferably in the range from 2% to 9% by weight after drying and before application of the post-crosslinking solution. Optionally, however, this moisture content can also be raised up to 75% by weight, for example by applying water in an upstream spraying mixer. The moisture content is determined by EDANA (European Disposables and Nonwovens Association) recommended test method No. WSP 230.2-05 "Moisture content". Such an increase in the moisture content leads to a slight preswelling of the base polymer and improves the distribution of the crosslinker on the surface and also the penetration through the polymeric particles.

Spray nozzles useful in the process of the present invention are not subject to any restriction. Suitable nozzles and atomizing systems are described for example in the following literature references: Zerstauben von Flussigkeiten, Expert-Verlag, volume 660, Reihe Kontakt & Studium, Thomas Richter (2004) and also in Zerstaubungstechnik, Springer-Verlag, VDI-Reihe, Gunter Wozniak (2002). Mono- and polydisperse spraying systems can be used. Suitable polydisperse systems include one-material pressure nozzles (forming a jet or lamellae), rotary atomizers, two-material atomizers, ultrasonic atomizers and impact nozzles. With regard to two-material atomizers, the mixing of the liquid phase with the gas phase can take place not only internally but also externally. The spray pattern produced by the nozzles is not critical and can assume any desired shape, for example a round jet, flat jet, wide angle round jet or circular ring. The use of a non-oxidizing gas is advantageous when two-material atomizers are used, particular preference being given to nitrogen, argon or carbon dioxide. Such nozzles can be pressure fed with the liquid to be spray dispensed. The atomizing of the liquid to be spray dispensed can in this case be effected by decompressing the liquid in the nozzle bore after the liquid has reached a certain minimum velocity. Also useful for the purpose of the invention are one-material nozzles, for example slot nozzles or swirl or whirl chambers (full cone nozzles) (available for example from Dusen-Schlick GmbH, Germany or from Spraying Systems Deutschland GmbH, Germany). Such nozzles are also described in EP 0 534 228 A1 and EP 1 191 051 A2.

After spraying, the polymeric particles are thermally postcrosslinked.

The spraying with the solution of postcrosslinker is preferably carried out in mixers having moving mixing implements, such as screw mixers, paddle mixers, disk mixers, plowshare mixers and shovel mixers. Particular preference is given to vertical mixers and very particular preference to plowshare mixers and shovel mixers. Useful mixers include for example Lödige mixers, Bepex mixers, Nauta mixers, Processall mixers and Schugi mixers.

Contact dryers are preferable, shovel dryers more preferable and disk dryers most preferable as apparatus in which thermal postcrosslinking is carried out. Suitable dryers include for example Bepex dryers and Nara dryers. Fluidized bed dryers, for example Carman dryers, can be used as well.

Thermal postcrosslinking can take place in the mixer itself, for example by heating the shell or blowing hot inert gases into it. It is similarly possible to use a downstream dryer, for example a tray dryer, a rotary tube oven or a heatable screw. But it is also possible for example to utilize an azeotropic distillation as a drying process.

It is particularly preferable to apply the solution of postcrosslinker in a high speed mixer, for example of the Schugi-Flexomix or Turbolizer type, to the base polymer and the latter can then be thermally postcrosslinked in a reaction dryer, for example of the Nara-Paddle-Dryer type or a disk dryer. The base polymer used can still have a temperature in the range from 10 to 120° C. from preceding operations, and the postcrosslinker solution can have a temperature in the range from 0 to 150° C. More particularly, the postcrosslinker solution can be heated to lower the viscosity. The preferred postcrosslinking and drying temperature range is from 30 to 220° C., especially from 120 to 210° C. and most preferably from 145 to 190° C. The preferred residence time at this temperature in the reaction mixer or dryer is below 100 minutes, more preferably below 70 minutes and most preferably below 40 minutes. When a fluidized bed dryer is used, the residence time is preferably below 30 minutes, more preferably below 20 minutes and most preferably below 10 minutes.

The postcrosslinking dryer in the process of the present invention is preferably purged with an inert gas during the thermal postcrosslinking reaction in order that the vapors may be removed and oxidizing gases, such as atmospheric oxygen, may be displaced. To augment the drying process, the dryer and the attached assemblies are thermally well-insulated and ideally fully heated.

Suitable inert gases are for example nitrogen, carbon dioxide, argon, water vapor, of which nitrogen is preferred. The inert gas rate is preferably in the range from 0.0001 to 10 m$^3$, preferably in the range from 0.001 to 5 m$^3$, more preferably in the range from 0.005 to 1 m$^3$ and most preferably in the range from 0.005 to 0.1 m$^3$ based on 1 kg of water-absorbing polymeric particles.

Inert gases in the process of the present invention are entities which are present in gaseous form at the postcrosslinking temperature and given pressure in the postcrosslinking dryer and which under these conditions do not have an oxidizing effect on the constituents of the drying polymeric particles.

To produce very white polymeric particles, the gas space in the dryer is kept as free as possible of oxidizing gases in the process of the present invention.

It is possible according to the present invention to heat the polymeric particles via contact surfaces in the dryer or via added warm inert gas, or via a mixture of one or more inert gases with water vapor, or with water vapor alone. When the heat is supplied via contact surfaces it is possible to carry out the reaction under inert gas at slight or complete underpressure. When water vapor is used to directly heat the polymeric particles, it is desirable according to the present invention to operate the dryer at atmospheric pressure or overpressure. In this case it can be sensible to split the postcrosslinking step into a heating step and a reaction step under inert gas but without water vapor. This can be actualized in one or more apparatuses. According to the present invention, the polymeric particles can be heated with water vapor in the postcrosslinking mixer.

In the process of the present invention, the inert gas can be blown, if it does not comprise water vapor, into the postcrosslinking dryer via nozzles, but it is particularly preferable to add the inert gas to the polymeric particle stream in or shortly upstream of the postcrosslinking mixer, via nozzles. For example, the oxygen content in the atmosphere of the postcrosslinking dryer or of the postcrosslinking mixer can be policed via oxygen probes.

Cosolvents removed with the vapors may of course be condensed again outside the postcrosslinking dryer and if appropriate recycled.

After the thermal postcrosslinking has been concluded, the dried water-absorbing polymeric particles are cooled. To this end, the warm and dry polymeric particles are preferably continuously transferred into a downstream cooler. This can be for example a disk cooler, a Nara paddle cooler or a screw cooler. Cooling is via the walls and if appropriate the stirring elements of the cooler, through which a suitable cooling medium such as for example warm or cold water flows. Selectively, however, a fluidized bed cooler may also be used. Water or aqueous solutions of additives may preferably be sprayed on in the cooler, for example the metal salts according to the invention as an aqueous solution; this increases the efficiency of cooling (partial evaporation of water) and the residual moisture content in the finished product can be adjusted to a value in the range from 0% to 6% by weight, preferably in the range from 0.01% to 4% by weight and more preferably in the range from 0.1% to 3% by weight. The increased residual moisture content reduces the dust content of the product.

Optionally, however, it is possible to use the cooler for cooling only and to carry out the addition of water and additives in a downstream separate mixer. Cooling stops the reaction by lowering the temperature to below the reaction temperature and the temperature needs altogether only to be lowered to such an extent that the product is easily packable into plastic bags or into silo trucks.

Optionally, however, all known coatings, such as film-forming polymers, thermoplastic polymers, dendrimers, polycationic polymers (such as polyvinylamine, polyethyleneimine or polyallylamine), water-insoluble polyvalent metal salts, such as magnesium carbonate, magnesium oxide, magnesium hydroxide, calcium carbonate, calcium sulfate or calcium phosphate, any water-soluble mono- or polyvalent metal salts known to a one skilled in the art, such as aluminum sulfate, sodium, potassium, zirconium or iron salts, or hydrophilic inorganic particles, such as clay minerals, fumed silica, alumina and magnesia, can be additionally applied. This makes it possible to achieve additional effects, such as a reduced tendency to cake, improved processing properties or a further enhanced Saline Flow Conductivity (SFC). When the additives are used and sprayed in the form of dispersions, they are preferably used as aqueous dispersions, and it is preferable to additionally apply a dustproofing agent to fix the additive on the surface of the water-absorbing polymer. The dustproofing agent is then added directly to the dispersion of the inorganic pulverulent additive, but optionally it can be added as a separate solution before, during or after the application of the inorganic pulverulent additive, by spraying. The concurrent spraying with postcrosslinking agent, dustproofing agent and pulverulent inorganic additive in postcrosslinking is most preferable. In a further preferred version of the process, however, the dustproofing agent is added separately in the cooler, for example by spraying from top, bottom or from the side. Particularly suitable dustproofing agents which can also serve to fix pulverulent inorganic additives to the surface of the water-absorbing polymeric particles are polyethylene glycols having a molecular weight in the range from 400 to 20000 g/mol, polyglycerol, 3- to 100-tuply ethoxylated polyols, such as trimethylolpropane, glycerol, sorbitol and neopentylglycol. Of particular suitability are 7- to 20-tuply ethoxylated glycerol or trimethylolpropane, such as for example Polyol TP 70® (Perstorp, Sweden). The latter have the particular advantage that they only insignificantly lower the surface tension of an aqueous extract of the water-absorbing polymeric particles.

In a particularly preferred embodiment of the invention, postcrosslinker (preferably 2-oxazolidone or N-(2-hydroxyethyl)-2-oxazolidone and/or 1,3-propanediol), organic solvent (preferably isopropanol), aluminum lactate and if appropriate some surfactant (preferably Span® 20) are suspended with water and then applied by means of a spray mixer (preferably Schugi-Mix) to the polymeric particles by means of a two-material nozzle or a one-material nozzle, not only the spray mixer but also the downstream thermal postcrosslinking being purged with inert gas (preferably nitrogen) such that the oxygen volume fraction in these assemblies is less than 14% by volume, preferably lower than 10% by volume, more preferably less than 5% by volume and most preferably less than 1% by volume.

In a further particularly preferred embodiment of the invention, postcrosslinker (preferably 2-oxazolidone or N-(2-hydroxyethyl)-2-oxazolidone and/or 1,3-propanediol), organic solvent (preferably isopropanol), aluminum lactate and if appropriate some surfactant (preferably Span® 20) are suspended with water and then applied by means of a spray mixer (preferably Schugi-Mix) to the polymeric particles by means of a two-material nozzle or a one-material nozzle, not only the spray mixer but also the downstream thermal postcrosslinker being purged with inert gas (preferably nitrogen) such that the oxygen volume fraction in these assemblies is less than 14% by volume, preferably lower than 10% by volume, more preferably less than 5% by volume and most preferably less than 1% by volume. A separate feed line is used to spray dispense, concurrently to this poscrosslinking solution, a saturated aqueous solution of calcium hydroxide with solid calcium hydroxide finely dispersed therein.

In yet a further particularly preferred embodiment of the invention, postcrosslinker (preferably ethyleneglycoldiglycidylether or 2-oxazolidone or N-(2-hydroxyethyl)-2-oxazolidone and/or 1,3-propanediol and/or 1,2-propanediol), if appropriate organic solvent (preferably isopropanol), an aqueous calcium salt (preferably calcium lactate) and aluminum lactate and aluminum lactate and if appropriate some surfactant (preferably Span® 20) are suspended with water and then applied by means of a spray mixer (preferably Schugi-Mix) to the polymer by means of a two-material nozzle or a one-material nozzle, not only the spray mixer but also the downstream postcrosslinker being purged with inert gas (preferably nitrogen) such that the oxygen volume fraction in these assemblies is less than 14% by volume, preferably lower than 10% by volume, more preferably less than 5% by volume and most preferably less than 1% by volume.

The present invention further provides the water-absorbing polymeric particles obtainable according to the process of the present invention.

The water-absorbing polymeric particles of the present invention typically have a centrifuge retention capacity (CRC) of at least 25 g/g, preferably of at least 26 g/g, more preferably of at least 27 g/g, even more preferably at least 28 g/g and most preferably at least 29 g/g and customarily not above 40 g/g. Centrifuge retention capacity (CRC) is determined by EDANA (European Disposables and Nonwovens Association) recommended test method No. WSP 241.2-05 "Centrifuge retention capacity".

The water-absorbing polymeric particles of the present invention typically have an absorbency under a load of 4.83 kPa (AUL0.7 psi) of at least 21 g/g, preferably at least 22 g/g, more preferably at least 23 g/g, even more preferably at least 24 g/g and most preferably at least 25 g/g and customarily not above 30 g/g. Absorbency under load (AUL0.7 psi) is determined similarly to EDANA (European Disposables and Nonwovens Association) recommended test method No. WSP 2422.2-05 "Absorption under pressure".

The water-absorbing polymeric particles of the present invention typically have a saline flow conductivity (SFC) of at least $30 \times 10^{-7}$ cm$^3$ s/g, preferably at least $45 \times 10^{-7}$ cm$^3$ s/g, even more preferably at least $80 \times 10^{-7}$ cm$^3$ s/g, even more preferably at least $100 \times 10^{-7}$ cm$^3$ s/g and most preferably at least $140 \times 10^{-7}$ cm$^3$ s/g, and customarily not above $700 \times 10^{-7}$ cm$^3$ s/g.

The process of the present invention provides water-absorbing polymeric particles of high whiteness. The water-absorbing polymeric particles obtained can be stored at elevated ambient temperature and high relative humidity and color degrade very slowly compared with normal water-absorbing polymeric particles and therefore have better storability and longer utility as polymeric particles and, after processing, as hygiene articles. More particularly, water-absorbing polymeric particles coated with both salts (calcium salt and aluminum salt have high saline flow conductivity (SFC) coupled with high absorptive performance (CRC and AUL0.7 psi) and also good color stability and high whiteness.

The L value of the white polymeric particles in the unstored state is typically at least 75, preferably at least 80, more preferably at least 85, most preferably at least 90, and not more than 100.

The a value of the white polymeric particles in the unstored state is typically in the range from −2.5 to +2.5, preferably in the range from −2.0 to +2.0, more preferably in the range from −1.5 to +1.5 and most preferably in the range from −0.5 to +0.5.

The b value of the white polymeric particles in the unstored state is typically in the range from 0 to 10, preferably in the range from 2 to 8, more preferably in the range from 3 to 7 and most preferably in the range from 4 to 6.5.

After "storage testing" at elevated temperature and high relative humidity, the water-absorbing polymeric particles of the present invention are measured for their L and a values and are found to have results in the region of the samples in the unstored state, and after 100 hours of storage still have b values of preferably not more than 12 and more preferably of not more than 10, and also after 300 hours of storage have b values of preferably not more than 15 and more preferably of not more than 12. A b value above 12 is critical in feminine hygiene articles and ultrathin diapers; a b value of more than 15 is even critical in customary diapers, since this degree of color degradation can be perceived by the consumer in use.

Furthermore, the water-absorbing polymeric particles of the present invention are substantially free of compounds which lead to unpleasant odors during use in particular.

The present invention further provides hygiene articles comprising water-absorbing polymeric particles according to the present invention, preferably ultrathin diapers comprising an absorbent layer consisting of 50% to 100% by weight, preferably 60% to 100% by weight, more preferably 70% to 100% by weight, even more preferably 80% to 100% by weight and most preferably 90% to 100% by weight of water-absorbing polymeric particles according to the present invention, the envelope surrounding the absorbent layer not included of course.

The water-absorbing polymeric particles of the present invention are also very advantageous for producing laminates and composite structures as described for example in US 2003/0181115 and US 2004/0019342. As well as the hotmelt adhesives described in the two references for producing such novel absorbent structures, and especially the hotmelt adhesive fibers which are described in US 2003/0181115 and to which the water-absorbing polymeric particles is bound, the water-absorbing polymeric particles of the present invention are also useful for producing completely analogous structures by utilizing UV crosslinkable hotmelt adhesives which are marketed for example as AC-Resin® (BASF AG, Germany). These UV crosslinkable hotmelt adhesives have the advantage of being possible at as low as 120 to 140° C.; therefore, they have better compatibility with many thermoplastic substrates. It is a further significant advantage that UV crosslinkable hotmelt adhesives are generally recognized as very safe by toxicologists and do not cause any outgassing in hygiene articles. A very significant advantage in connection with the water-absorbing polymeric particles of the present invention is the property of UV crosslinkable hotmelt adhesives not to yellow during processing and crosslinking. This is advantageous especially when ultrathin or partially transparent hygiene articles are to be produced. The combination of the water-absorbing polymeric particles of the present invention with UV crosslinkable hotmelt adhesives is therefore particularly advantageous. Suitable UV crosslinkable hotmelt adhesives are described for example in EP 0 377 199 A2, EP 0 445 641 A1, U.S. Pat. No. 5,026,806, EP 0 655 465 A1 and EP 0 377 191 A2.

To determine the quality of postcrosslinking, the dried water-absorbing polymeric particles are tested using the test methods described hereinbelow.

Methods:

The measurements should be carried out, unless otherwise stated, at an ambient temperature of 23±2° C. and a relative humidity of 50±10%. The water-absorbing polymeric particles are thoroughly mixed through before measurement.

Centrifuge Retention Capacity (CRC)

Centrifuge Retention Capacity is determined by EDANA (European Disposables and Nonwovens Association) recommended test method No. WSP 241.5-0.2 "Centrifuge retention capacity".

Absorbency Under Load (AUL0.3 psi)

Absorbency under a load of 2.07 kPa (0.3 psi) is determined for the water-absorbing polymeric particles by EDANA (European Disposables and Nonwovens Association) recommended test method No. WSP 242.2-05 "Absorption under pressure".

Absorbency Under Load (AUL0.7 psi)

Absorbency under a load of 4.83 kPa (0.7 psi) is determined for the water-absorbing polymeric particles by EDANA (European Disposables and Nonwovens Association) recommended test method No WSP 242.2-05 "Absorption under pressure", using a weight of 49 g/cm$^2$ (0.7 psi) instead of a weight of 21 g/cm$^2$ (0.3 psi).

Saline Flow Conductivity (SFC)

The flow conductivity of a swollen layer of gel under a confining pressure of 0.3 psi (2070 Pa) is determined as described in EP 0 640 330 A1 as the Gel Layer Permeability of a swollen gel layer of water-absorbing polymeric particles, although the apparatus described in the aforementioned patent application at page 19 and FIG. 8 was modified to the effect that the glass frit (40) is no longer used, the piston (39) is made of the same plastics material as the cylinder (37) and now comprises 21 equally sized holes uniformly distributed over the entire contact surface. The procedure and evaluation of the measurement remains unchanged compared to EP 0 640 330 A1. The flow rate is automatically recorded.

Saline Flow Conductivity (SFC) is calculated as follows:

$$\text{SFC [cm}^3\text{ s/g]} = (Fg(t=0) \times L0)/(d \times A \times WP),$$

where Fg(t=0) is the flow rate of NaCl solution in g/s obtained from a linear regression analysis of the Fg(t) data of the flow rate determinations by extrapolation to t=0, L0 is the thickness of the gel layer in cm, d is the density of the NaCl solution in g/cm$^3$, A is the area of the gel layer in cm$^2$ and WP is the hydrostatic pressure on the gel layer in dyn/cm$^2$.

16 h Extractables

The level of extractable constituents in the water-absorbing polymeric particles is determined by the EDANA (European Disposables and Nonwovens Association) recommended test method No. WSP 241.2-05 "Extractables".

Moisture Content of Hydrogel

The water content of the water-absorbing polymeric particles is determined by the EDANA (European Disposables and Nonwovens Association) recommended test method No. WSP 230.2-05 "Moisture content".

CIE Color Number (L a b)

Color measurement was carried out in accordance with the CIELAB procedure (Hunterlab, volume 8, 1996, issue 7, pages 1 to 4). In the CIELAB system, the colors are described via the coordinates L, a and b of a three-dimensional system. L indicates lightness, with L=0 denoting black and L=100 denoting white. The a and b values indicate the position of the color on the color axes red/green and yellow/blue respectively, where +a represents red, −a represents green, +b represents yellow and −b represents blue.

The color measurement complies with the three-range method of German standard specification DIN 5033-6.

A LabScan XE S/N LX17309 (HunterLab, Reston, US) calorimeter was used.

Storage Testing

Measurement 1: A glass dish 9 cm in internal diameter and 1.5 cm in height is overfilled with water-absorbing polymeric particles and then smoothed off flat with a knife across the rim and the CIE color numbers are determined.

Measurement 2: A glass dish 9 cm in internal diameter and 1.5 cm in height is overfilled with water-absorbing polymeric particles and then smoothed off flat with a knife across the rim. The dish is covered with a fitting glass lid and the CIE color numbers are determined.

Measurement 3 and storage: A glass dish 9 cm in internal diameter and 1.5 cm in height is filled with 30 g of water-absorbing polymeric particles and then smoothed off. The dish is then placed without a lid in a heated conditioning cabinet at constant relative humidity. The particles swell somewhat in the process and are subjected to these atmospheric conditions for a predetermined period. Storage takes place at 60° C. and 90% relative humidity.

After expiration of the storage, time, the dish is removed, covered with a fitting glass lid and the CIE color numbers are determined.

The EDANA test methods are obtainable for example at European Disposables and Nonwovens Association, Avenue Eugene Plasky 157, B-1030 Brussels, Belgium.

EXAMPLES

Example 1 (Comparative)

A Lödige VT 5R-MK plowshare kneader 5 l in capacity was charged with 459 g of water, 213.9 g of acrylic acid (stabilized with 0.02% by weight of hydroquinone monomethyl ether), 1924.9 g of 37.3% by weight sodium acrylate solution (100 mol % neutralized) which had previously been filtered through activated carbon to remove hydroquinone monomethyl ether, and also 2.52 g of 3-tuply ethoxylated glycerol triacrylate. The initial charge was inertized for 20 minutes by bubbling nitrogen through it. The hydroquinone monomethyl ether content, based on acrylic acid, was about 0.005% by weight. The reaction mixture was cooled from the outside such that the subsequent addition of initiator took place at about 20° C. Finally, 2.139 g of sodium persulfate (dissolved in 12.12 g of water), 0.046 g of ascorbic acid (dissolved in 9.12 g of water) and 0.127 g of 30% by weight hydrogen peroxide (dissolved in 1.15 g of water) were rapidly added in succession into the kneader with stirring. The reaction ensued speedily and when an internal temperature of 30° C. was reached the jacket was heated with hot heat transfer medium at 80° C. in order that the reaction may be completed under as nearly adiabatic conditions as possible. After attainment of the maximum temperature, cooling fluid (−12° C.) was then used to cool down the resultant gel to below 50° C. before it was discharged.

The gel was distributed onto two wire-bottomed metal trays and dried in a vacuum drying cabinet at 140° C. and 250 mbar. This was followed by comminution using an ultracentrifugal mill before the product was classified to a particle size from 150 to 850 µm by sieving off under- and oversize.

The base polymer thus prepared had the following properties:
CRC=36.5 g/g
AUL0.3 psi=8.3 g/g
16 h extractables=12.8% by weight
Residual moisture content=2.6% by weight

| Color number | Measurement 1 | Measurement 2 | Measurement 3 (after 100 h) | Measurement 3 (after 300 h) |
| --- | --- | --- | --- | --- |
| L | 91.2 | 86.2 | 76.0 | 70.0 |
| a | −1.3 | −1.8 | 0.8 | 2.5 |
| b | 6.9 | 7.2 | 11.5 | 16.0 |

Example 2 (Comparative)

20 g of the base polymer prepared in Example 1 were sprayed with a postcrosslinker solution, consisting of 0.02 g of N-(2-hydroxyethyl)-2-oxazolidinone, 0.60 g of water and 0.30 g of 1,3-propanediol, by means of a syringe in a Waring laboratory mixer at medium stirring level. The moist polymeric particles were additionally homogenized with a spatula and then uniformly distributed in a Petri dish having an internal diameter of 18.5 cm and heat treated at 175° C. in a vacuum drying cabinet (Heraeus VACUTHERM VT 6060M; Kendro Laboratory Products GmbH, Germany) for 60 minutes. In the process, the polymeric particles were overlaid with about 1200 l/h of nitrogen at about 1013 mbar, producing an oxygen partial pressure of <10 mbar.

The postcrosslinked polymeric particles were freed of lumps by passing them through an 850 µm sieve, and analyzed.

The postcrosslinked polymeric particles thus produced had the following properties:
CRC=31.0 g/g
AUL0.7 psi=24.5 g/g
SFC=30×10$^{-7}$ cm$^3$ s/g

| Color number | Measurement 1 | Measurement 2 | Measurement 3 (after 100 h) | Measurement 3 (after 300 h) |
| --- | --- | --- | --- | --- |
| L | 89.2 | 84.3 | 73.9 | 65.0 |
| a | −1.0 | −1.5 | 2.1 | 4.5 |
| b | 7.9 | 8.2 | 13.5 | 20.5 |

Example 3 (Comparative)

20 g of the base polymer prepared in Example 1 were sprayed with a postcrosslinker solution, consisting of 0.02 g of N-(2-hydroxyethyl)-2-oxazolidinone, 0.60 g of water and 0.30 g of 1,3-propanediol and 0.20 g of calcium hydroxide dispersed in this solution, by means of a syringe in a Waring laboratory mixer at medium stirring level. The moist polymeric particles were additionally homogenized with a spatula and then uniformly distributed in a Petri dish having an internal diameter of 18.5 cm and heat treated at 175° C. in a vacuum drying cabinet (Heraeus VACUTHERM VT 6060M; Kendro Laboratory Products GmbH, Germany) for 60 minutes. In the process, the polymeric particles were overlaid with about 1200 l/h of nitrogen at about 1013 mbar, producing an oxygen partial pressure of <10 mbar.

The postcrosslinked polymeric particles were freed of lumps by passing them through an 850 µm sieve, and analyzed.

The postcrosslinked polymeric particles thus produced had the following properties:
CRC=30.7 g/g
AUL0.7 psi=24.2 g/g
SFC=35×10$^{-7}$ cm$^3$ s/g

| Color number | Measurement 1 | Measurement 2 | Measurement 3 (after 100 h) | Measurement 3 (after 300 h) |
| --- | --- | --- | --- | --- |
| L | 93.3 | 89.1 | 80.5 | 81.0 |
| a | −0.8 | −1.5 | 1.0 | 0.1 |
| b | 5.2 | 5.9 | 9.9 | 12.4 |

Example 4

20 g of the base polymer prepared in Example 1 were sprayed with a postcrosslinker solution, consisting of 0.02 g of N-(2-hydroxyethyl)-2-oxazolidinone, 0.60 g of water and 0.30 g of 1,3-propanediol and 0.20 g of calcium hydroxide dispersed in this solution, by means of a syringe in a Waring laboratory mixer at medium stirring level. Then, 0.48 g of an aqueous solution comprising 0.12 g of aluminum lactate was applied by spraying. The moist polymeric particles were additionally homogenized with a spatula and then uniformly distributed in a Petri dish having an internal diameter of 18.5 cm and heat treated at 175° C. in a vacuum drying cabinet (Heraeus VACUTHERM VT 606DM; Kendro Laboratory Products GmbH, Germany) for 60 minutes. In the process, the polymeric particles were overlaid with about 1200 l/h of nitrogen at about 1013 mbar, producing an oxygen partial pressure of <10 mbar.

The postcrosslinked polymeric particles were freed of lumps by passing them through an 850 µm sieve, and analyzed.

The postcrosslinked polymeric particles thus produced had the following properties:
CRC=30.4 g/g
AUL0.7 psi=24.5 g/g
SFC=50×10$^{-7}$ cm$^3$ s/g

| Color number | Measurement 1 | Measurement 2 | Measurement 3 (after 100 h) | Measurement 3 (after 300 h) |
| --- | --- | --- | --- | --- |
| L | 93.2 | 89.3 | 81.0 | 80.9 |
| a | −0.8 | −1.5 | 0.8 | 0.1 |
| b | 5.4 | 6.0 | 9.8 | 12.1 |

Example 5

The base polymer prepared in Example 1 was sized to 150 to 700 μm by sieving off under- and oversize. 20 g of the sized base polymer were sprayed with a postcrosslinker solution, consisting of 0.02 g of N-(2-hydroxyethyl)-2-oxazolidinone, 0.30 g of water and 0.30 g of 1,3-propanediol and 0.0006 g of Span® 20 by means of a syringe in a Waring laboratory mixer at medium stirring level. Subsequently, 1.3 g of an aqueous solution comprising 0.20 g of calcium lactate and 0.12 g of aluminum lactate were applied by spraying. The moist polymeric particles were additionally homogenized with a spatula and then uniformly distributed in a Petri dish having an internal diameter of 18.5 cm and heat treated at 175° C. in a vacuum drying cabinet (Heraeus VACUTHERM VT 606DM; Kendro Laboratory Products GmbH, Germany) for 90 minutes. In the process, the polymeric particles were overlaid with about 1200 l/h of nitrogen at about 1013 mbar, producing an oxygen partial pressure of <10 mbar.

The postcrosslinked polymeric particles were freed of lumps by passing them through a 700 μm sieve, and analyzed. The fraction of particles less than 150 μm was less than 0.3% by weight.

The postcrosslinked polymeric particles thus produced had the following properties:
CRC=29.0 g/g
AUL0.7 psi=24.2 g/g
SFC=130×10$^{-7}$ cm$^3$ s/g

| Color number | Measurement 1 | Measurement 2 | Measurement 3 (after 100 h) | Measurement 3 (after 300 h) |
|---|---|---|---|---|
| L | 90.5 | 86.6 | 80.0 | 78.0 |
| a | −0.9 | −1.2 | 0.1 | 0.2 |
| b | 5.2 | 5.8 | 9.6 | 11.7 |

Example 6

The base polymer prepared in Example 1 was sized to 150 to 600 μm by sieving off under- and oversize. 20 g of the sized base polymer were sprayed with a postcrosslinker solution, consisting of 0.02 g of N-(2-hydroxyethyl)-2-oxazolidinone, 0.30 g of water and 0.30 g of 1,3-propanediol and 0.0006 g of Span® 20 by means of a syringe in a Waring laboratory mixer at medium stirring level. Subsequently, 1.3 g of an aqueous solution comprising 0.20 g of calcium lactate and 0.12 g of aluminum lactate were applied by spraying. The moist polymeric particles were additionally homogenized with a spatula and then uniformly distributed in a Petri dish having an internal diameter of 18.5 cm and heat treated at 175° C. in a vacuum drying cabinet (Heraeus VACUTHERM VT 6060M; Kendro Laboratory Products GmbH, Germany) for 90 minutes. In the process, the polymeric particles were overlaid with about 1200 l/h of nitrogen at about 1013 mbar, producing an oxygen partial pressure of <10 mbar.

The postcrosslinked polymeric particles were freed of lumps by passing them through a 600 μm sieve, and analyzed. The fraction of particles less than 150 μm was less than 0.3% by weight.

The postcrosslinked polymeric particles thus produced had the following properties:
CRC=28.2 g/g
AUL0.7 psi=24.4 g/g
SFC=115×10$^{-7}$ cm$^3$ s/g

| Color number | Measurement 1 | Measurement 2 | Measurement 3 (after 100 h) | Measurement 3 (after 300 h) |
|---|---|---|---|---|
| L | 91.4 | 87.6 | 81.0 | 79.5 |
| a | −0.7 | −1.0 | 0.2 | 0.2 |
| b | 5.1 | 6.0 | 9.1 | 11.3 |

Example 7 (Comparative)

The base polymer prepared in Example 1 was sized to 150 to 600 μm by sieving off under- and oversize. 20 g of the sized base polymer were sprayed with a postcrosslinker solution, consisting of 0.02 g of N-(2-hydroxyethyl)-2-oxazolidinone, 0.30 g of water and 0.30 g of 1,3-propanediol and 0.0006 g of Spans 20 by means of a syringe in a Waring laboratory mixer at medium stirring level. Subsequently, 1.3 g of an aqueous solution comprising 0.05 g of aluminum lactate were applied by spraying. The moist polymeric particles were additionally homogenized with a spatula and then uniformly distributed in a Petri dish having an internal diameter of 18.5 cm and heat treated at 175° C. in a vacuum drying cabinet (Heraeus VACUTHERM VT 6060M; Kendro Laboratory Products GmbH, Germany) for 90 minutes. In the process, the polymeric particles were overlaid with about 1200 l/h of nitrogen at about 1013 mbar, producing an oxygen partial pressure of <10 mbar.

The postcrosslinked polymeric particles were freed of lumps by passing them through a 600 μm sieve, and analyzed. The fraction of particles less than 150 μm was less than 0.3% by weight.

The postcrosslinked polymeric particles thus produced had the following properties:
CRC=25.9 g/g
AUL0.7 psi=22.2 g/g
SFC=97×10$^{-7}$ cm$^3$ s/g

| Color number | Measurement 1 | Measurement 2 | Measurement 3 (after 100 h) | Measurement 3 (after 300 h) |
|---|---|---|---|---|
| L | 93.3 | 89.7 | 69.0 | 62.8 |
| a | −1.1 | −1.8 | 2.2 | 3.5 |
| b | 5.5 | 6.1 | 15.1 | 18.7 |

Example 8 (Comparative)

The base polymer prepared in Example 1 was sized to 150 to 600 μm by sieving off under- and oversize. 20 g of the sized base polymer were sprayed with a postcrosslinker solution, consisting of 0.02 g of N-(2-hydroxyethyl)-2-oxazolidinone, 0.30 g of water and 0.30 g of 1,3-propanediol and 0.0006 g of Spans 20 by means of a syringe Waring laboratory mixer at medium stirring level. Subsequently 0.7 g of aqueous dispersion, comprising 0.05 g of calcium hydroxide, and 0.6 g of aqueous solution, comprising 0.05 g of aluminum sulfate, were applied in succession by spraying. The moist polymeric particles were additionally homogenized with a spatula and then uniformly distributed in a Petri dish having an internal diameter of 18.5 cm and heat treated at 175° C. in a vacuum drying cabinet (Heraeus VACUTHERM VT 6060M; Kendro Laboratory Products GmbH, Germany) for 90 minutes. In the process, the polymeric particles were overlaid with about 1200 l/h of nitrogen at about 1013 mbar, producing an oxygen partial pressure of <10 mbar.

The postcrosslinked polymeric particles were freed of lumps by passing them through a 600 μm sieve, and analyzed. The fraction of particles less than 150 μm was less than 0.3% by weight.

The postcrosslinked polymeric particles thus produced had the following properties:
CRC=26.5 g/g
AUL0.7 psi=22.0 g/g
SFC=100×10$^{-7}$ cm$^3$ s/g

| Color number | Measurement 1 | Measurement 2 | Measurement 3 (after 100 h) | Measurement 3 (after 300 h) |
|---|---|---|---|---|
| L | 91.8 | 87.4 | 80.3 | 79.0 |
| a | −0.5 | −1.2 | 0.4 | 0.3 |
| b | 5.2 | 6.3 | 9.8 | 11.9 |

Example 9 (Comparative)

20 g of the base polymer prepared in Example 1 were sprayed with a postcrosslinker solution, consisting of 0.02 g of N-(2-hydroxyethyl)-2-oxazolidinone, 0.60 g of water and 0.30 g of 1,3-propanediol and also 0.04 g of aluminum sulfate by means of a syringe in a Waring laboratory mixer at medium stirring level. The moist polymeric particles were additionally homogenized with a spatula and then uniformly distributed in a Petri dish having an internal diameter of 18.5 cm and heat treated at 175° C. in a vacuum drying cabinet (Heraeus VACUTHERM VT 6060M; Kendro Laboratory Products GmbH, Germany) for 60 minutes. In the process, the polymeric particles were overlaid with about 1200 l/h of nitrogen at about 1013 mbar, producing an oxygen partial pressure of <10 mbar.

The postcrosslinked polymeric particles were freed of lumps by passing them through an 850 μm sieve, and analyzed.

The postcrosslinked polymeric particles thus produced had the following properties:
CRC=30.8 g/g
AUL0.7 psi=23.2 g/g
SFC=28×10$^{-7}$ cm$^3$ s/g

| Color number | Measurement 1 | Measurement 2 | Measurement 3 (after 100 h) | Measurement 3 (after 300 h) |
|---|---|---|---|---|
| L | 89.8 | 84.9 | 76.9 | 69.0 |
| a | −0.5 | −1.0 | 2.5 | 4.6 |
| b | 8.0 | 8.4 | 11.5 | 16.1 |

Example 10

20 g of the base polymer prepared in Example 1 were sprayed with a postcrosslinker solution, consisting of 0.02 g of N-(2-hydroxyethyl)-2-oxazolidinone, 0.80 g of water and 0.30 g of 1,3-propanediol and 0.10 g of aluminum lactate by means of a syringe in a Waring laboratory mixer at medium stirring level. The moist polymeric particles were additionally homogenized with a spatula and then uniformly distributed in a Petri dish having an internal diameter of 18.5 cm and heat treated at 175° C. in a vacuum drying cabinet (Heraeus VACUTHERM VT 6060M; Kendro Laboratory Products GmbH, Germany) for 60 minutes. In the process, the polymeric particles were overlaid with about 1200 l/h of nitrogen at about 1013 mbar, producing an oxygen partial pressure of <10 mbar.

The postcrosslinked polymeric particles were freed of lumps by passing them through an 850 μm sieve, and analyzed.

The postcrosslinked polymeric particles thus produced had the following properties:
CRC=30.1 g/g
AUL0.7 psi=24.7 g/g
SFC=47×10$^{-7}$ cm$^3$ s/g

| Color number | Measurement 1 | Measurement 2 | Measurement 3 (after 100 h) | Measurement 3 (after 300 h) |
|---|---|---|---|---|
| L | 93.3 | 89.8 | 80.0 | 79.8 |
| a | −1.1 | −1.8 | 0.9 | 0.3 |
| b | 5.5 | 6.1 | 9.2 | 14.7 |

We claim:

1. Water-absorbing polymeric particles prepared by polymerizing a monomer solution or suspension comprising
    a) at least one unsaturated carboxylic acid, optionally at least partially neutralized, and
    b) at least one hydroquinone monoether
    and coating the polymeric particles with at least one salt of a tervalent metal cation, wherein the salt of the tervalent metal cation is the salt of a carboxylic acid and/or a basic salt, and
    wherein the polymeric particles after 300 hours at 60° C. and a relative humidity of 90% have a b value of not more than 15.

2. The particles according to claim 1 wherein the unsaturated carboxylic acid a) is at least 25 mol % neutralized.

3. The particles according to claim 1 wherein the monomer solution comprises from 0.001% to 0.016% by weight of the hydroquinone monoether b), based on the unsaturated carboxylic acid a).

4. The particles according to claim 1 wherein the salt of the tervalent metal cation is a salt of a 2-hydroxy carboxylic acids.

5. The particles according to claim 1 wherein at least 90% by weight of the polymeric particles have a particle size in the range from greater than 150 to 600 μm.

6. The particles according to claim 1 wherein the polymeric particles are thermally postcrosslinked.

7. The particles according to claim 6 wherein the polymeric particles are coated with the salt of the tervalent metal cation prior to thermal postcrosslinking.

8. The particles according to claim 6 wherein the polymeric particles are coated with a basic salt of a bivalent metal cation prior to thermal postcrosslinking.

9. The particles according to claim 6 wherein a total partial pressure of one or more oxidizing gases in an atmosphere overlying the polymeric particles during thermal postcrosslinking is less than 140 mbar.

10. The particles according to claim 6 wherein coarse polymeric particles are removed before thermal postcrosslinking by a sieve having a mesh size of less than 700 μm.

11. The particles according to claim 6 wherein at least one 1,3-diol is used as a postcrosslinker.

12. The particles according to claim 6 wherein at least one cyclic carbamate is used as a postcrosslinker.

13. The particles according to claim 1 wherein the polymeric particles are further coated with at least one basic salt of a bivalent metal cation.

14. The particles according to claim 13 wherein the bivalent metal cation is a metal cation of the second main group of the periodic table.

15. The particles according to claim 13 wherein the polymeric particles are coated with a solution or suspension of the basic salt of the bivalent metal cation.

16. The particles according to claim 13 wherein the monomer solution comprises at least one inorganic peroxide c.

17. The particles according to claim 8 wherein the inorganic peroxide c) is a salt.

18. A hygiene article comprising water-absorbing polymeric particles of claim 1.

19. Water-absorbing polymeric particles prepared by polymerizing a monomer solution or suspension comprising
   a) at least one unsaturated carboxylic acid, optionally at least partially neutralized, and
   b) at least one hydroquinone monoether
   and coating the polymeric particles, said coating consisting essentially of at least one salt of a tervalent metal cation, wherein the salt of the tervalent metal cation is the salt of a carboxylic acid and/or a basic salt, and
   wherein the polymeric particles after 300 hours at 60° C. and a relative humidity of 90% have a b value of not more than 15.

20. The particles according to claim 19 wherein the polymeric particles are thermally postcrosslinked.

21. Water-absorbing polymeric particles prepared by polymerizing a monomer solution or suspension comprising
   a) at least one unsaturated carboxylic acid, optionally at least partially neutralized, and
   b) at least one hydroquinone monoether
   and coating the polymeric particles, said coating consisting essentially of
      i) at least one salt of a tervalent metal cation, wherein the salt of the tervalent metal cation is the salt of a carboxylic acid and/or a basic salt, and
      ii) with at least one basic salt of a bivalent metal cation,
   wherein the polymeric particles after 300 hours at 60° C. and a relative humidity of 90% have a b value of not more than 15.

22. The particles according to claim 21 wherein the polymeric particles are thermally postcrosslinked.

* * * * *

UNITED STATES PATENT AND TRADEMARK OFFICE
CERTIFICATE OF CORRECTION

PATENT NO. : 8,314,173 B2  Page 1 of 1
APPLICATION NO. : 12/521953
DATED : November 20, 2012
INVENTOR(S) : Riegel et al.

It is certified that error appears in the above-identified patent and that said Letters Patent is hereby corrected as shown below:

In the Claims

Column 29, Line 13, in Claim 16, delete "peroxide c." and insert -- peroxide c). --, therefor.

Column 29, Line 14, in Claim 17, delete "claim 8" and insert -- claim 16 --, therefor.

Signed and Sealed this
Twenty-first Day of October, 2014

Michelle K. Lee
*Deputy Director of the United States Patent and Trademark Office*